United States Patent [19]

Gomez

[11] Patent Number: 4,867,148

[45] Date of Patent: Sep. 19, 1989

[54] NONFILTERING FACIAL SEPARATION BARRIER

[76] Inventor: Gustavo J. Gomez, 175 E. 13th St., Hialeah, Fla. 33010

[21] Appl. No.: 410,058

[22] Filed: Aug. 20, 1982

[51] Int. Cl.$^4$ .......................... A61F 5/56; A61M 16/00
[52] U.S. Cl. ................................ 128/858; 128/202.28; 128/266.21; 128/859
[58] Field of Search ...................... 128/205.27, 205.29, 128/206.12, 206.13, 206.14, 206.16, 206.19, 202.21, 207.11, 139, 136

[56] References Cited

U.S. PATENT DOCUMENTS 1,297,842  3/1919  Harllee ................................ 128/126

FOREIGN PATENT DOCUMENTS 241987   9/1969   U.S.S.R. .......................... 128/206.16
21119    of 1909  United Kingdom ........... 128/206.16

Primary Examiner—Edward M. Coven
Assistant Examiner—Kim Reichle
Attorney, Agent, or Firm—Robert J. VanDerWall

[57] ABSTRACT

This invention is comprised of a nonfiltering facial separation barrier, configured to cover the mouth of a user, and is used for training purposes in cardiopulmonary resuscitation. It is formed of a relatively coarse mesh material and serves to prevent actual contact of the user's mouth with the training mannequin, while allowing a sufficient flow of air therethrough for resuscitation, with no effective filtration of air.

5 Claims, 1 Drawing Sheet

NONFILTERING FACIAL SEPARATION BARRIER

BACKGROUND OF THE INVENTION

The present invention relates to the field of facial coverings having sanitary function and, more particularly to a nonfiltering facial separation barrier constructed of a flexible mesh material which permits a free flow of air therethrough which is held in place over the mouth by elastic strap or cotton tie-on means. The device is used in cardiopulmonaryresuscitation training and prevents actual contact of the user's mouth with the training mannequin.

Of course, since the inventive barrier is used in training rather than actually in rescue efforts, the term "victim" as used herein really refers to the resuscitation mannequin rather than the victim, in such training.

Prior inventive effort in the field of facial coverings would appear to be completely devoid of those that do not seek to filter air passing through same, and most prior art appears limited to protective masks covering both the mouth and the nose of the user The prior art disclosed by a pre-examination search in this case consists of N. L. Brunner, U.S. Letters Pat. No. 2,281,744; E. S. Reitano, U.S. Letters Pat. No. 2,494,406; R. J. Wold, U.S. Letters Pat. No. 2,905,173; W. H. Bird, U.S. Letters Pat. No. 3,802,429; and J. A. Britton, U.S. Letters Pat. No. 1,150,991. All claim or imply filtering capability. All would necessarily restrict air flow rate as a price to be paid for such filtration, and such restricted flow rate and the greatly increased pressure drop across such prior art masks is unacceptable to the present invention, likely resulting in hyperventilation of the user. In the present invention, the nose of the user should not be covered so that air may be taken into the user's lungs in an unrestricted manner, to then be readily expelled through the mesh of the inventive device into the lungs of the "victim".

SUMMARY OF THE INVENTION

With the foregoing in mind, it is one of the principal objects of the present invention to provide a nonfiltering facial separation barrier to cover the mouth area of a user, but not the nose of the user.

A further object of the invention is to provide a facial separation barrier which is constructed of an open mesh material which permits a free flow of air therethrough, without filtration.

Yet another object of the present invention is to provide a separation barrier for use in training for cardiopulmonary resuscitation, and which prevents actual contact of the user's mouth with the victim's nose or mouth.

DESCRIPTION OF THE DRAWINGS

In accordance with the present invention there is provided a loose or open mesh nonfiltering facial separation barrier configured to cover the mouth, but not the nose, of the user and serving to prevent actual contact of the user's mouth with the victim's nose or mouth. The mask allows a sufficient flow of air therethrough for cardiopulmonary resuscitation training activities, without filtering of air.

The invention will be better understood after reading the following detailed description of the embodiments thereof with reference to the appended drawings, in which.

DESCRIPTION OF A PREFERRED EMBODIMENT OF THE INVENTION

Figure 1:
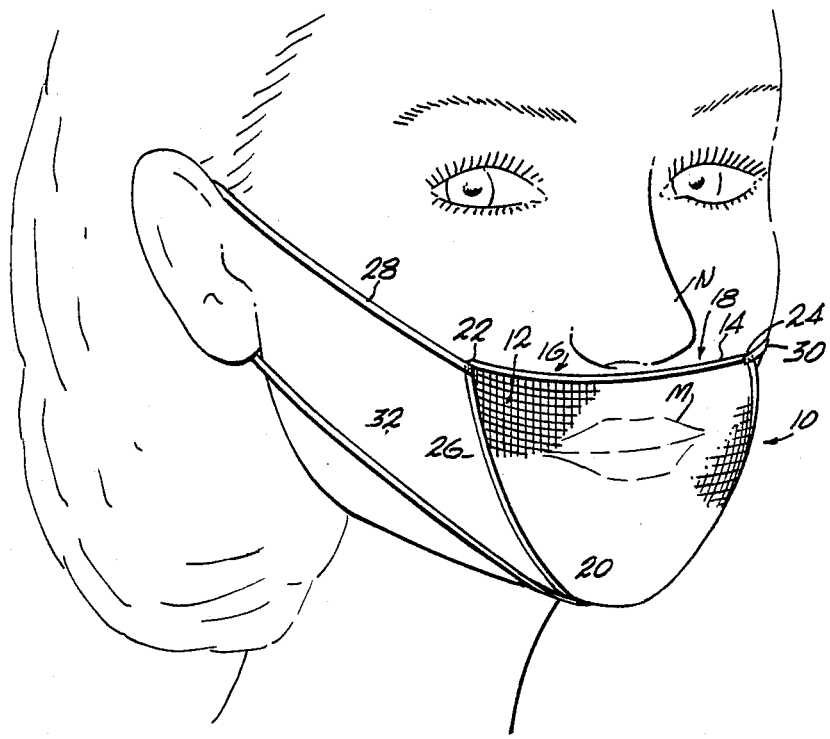
FIG. 1 is a perspective view of the nonfiltering facial separation barrier of the present invention, in place over the mouth area of a user.
Figure 2:
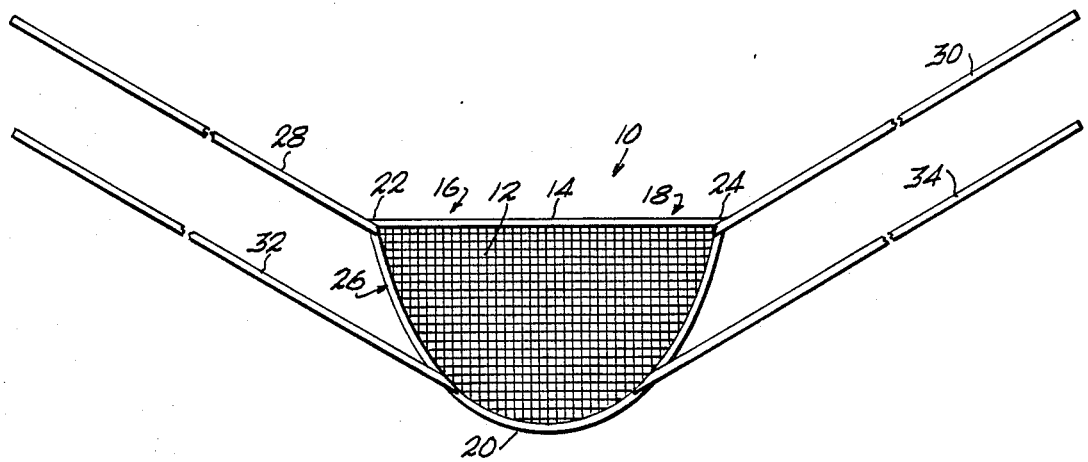
FIG. 2 is a plan view of the barrier of FIG. 1.

With reference to the drawings, the nonfiltering facial separation barrier of the present invention, indicated generally at 10, is illustrated in position in a covering relation to a user's mouth M, and includes a flexible sheet of covering material 12, comprised of an open mesh having openings of not less than one-eighth of an inch to permit a freeflow of air therethrough. In a preferred form, the top edge 14 of the barrier 10 is generally straight, to pass beneath the nose N of the user, and to extend opposite and outwardly from the nose as at 16, 18, a predetermined distance beyond the opposed corners of the mouth.

It will be seen that the large openings in the mesh of one-eighth of an inch or greater effectively precludes any filtration of germs, viruses, bacteria, and that the mesh is, therefore, solely for the purpose of preventing actual contact between the training mannequin and the user. The large openings also prevent the creation of a pressure drop across the mesh which is undesirable.

While the actual contour of the barrier 10 may be varied, in the form illustrated in the drawings, the side and bottom edges thereof define a generally curved configuration 20, extending a substantial distance outwardly and downwardly around the mouth M, from the top corners 22, 24.

A border strip 26 is secured about the edges of the barrier 10, and may be formed of an elastic tape material which readily conforms to the contour of the face area over which it passes.

Upper and lower pairs of securing straps 28, 30 and 32, 34 are secured respectively to the corners 22, 24 and lower edge of the curved portions of the barrier 10. The straps may be of a cotton tie-on or elastic strap type. The respective pairs of straps 28, 30 and 32, 24 pass rearwardly along respective sides of the user's face, one pair passing above the ears and the other pair passing below the ears as illustrated in FIG. 1.

Having described the presently preferred embodiment of the invention it should be understood that various changes in construction and arrangement will be apparent to those skilled in the art and are fully contemplated herein without departing from the true spirit of the invention. Accordingly, there is covered all alternatives, modifications and equivalents as may be included within the spirit and scope of the invention as defined by the appended claims.

What is claimed is:

1. A nonfiltering facial separation barrier comprising a sheet of flexible mesh material of a type to permit freeflow of air therethrough, having openings of not less than one-eighth of an inch, said sheet being sized to overlie a predetermind skin area about the mouth of a user, beneath the nose, said sheet being configured to contact, conform to contours of, and cover the mouth such that a substantially airtight seal can be maintained between the mouth of the user and an orifice in a training mannequin; and means to maintain the barrier in position on the user's face.

2. The nonfiltering facial separation barrier as defined in claim 1 wherein said means to maintain comprises upper and lower pairs of straps, having first ends secured relative to a periphery of said mesh material and extending outwardly therefrom for fixed engagement about the user's head.

3. The nonfiltering facial separation barrier as defined in claim 2 wherein said straps are formed of a suitable elastic material.

4. The nonfiltering facial separation barrier as defined in claim 1 including a border strip fixed about the periphery of said sheet of mesh material.

5. The nonfiltering facial separation barrier as defined in claim 4 wherein said border strip is formed of a suitable elastic material.

* * * * *